United States Patent
Szente

(10) Patent No.: US 9,790,351 B2
(45) Date of Patent: Oct. 17, 2017

(54) FAT-BINDING COMPOSITIONS

(75) Inventor: Lajos Szente, Budapest (HU)

(73) Assignee: Eastpond Laboratories Limited (IM)

( * ) Notice: Subject to any disclaimer, the term of this patent is extended or adjusted under 35 U.S.C. 154(b) by 0 days.

(21) Appl. No.: 13/046,762

(22) Filed: Mar. 13, 2011

(65) Prior Publication Data

US 2011/0224168 A1 Sep. 15, 2011

Related U.S. Application Data

(60) Provisional application No. 61/313,734, filed on Mar. 13, 2010.

(51) Int. Cl.

| | | |
|---|---|---|
| C08B 3/00 | (2006.01) |
| C08B 5/00 | (2006.01) |
| C08B 7/00 | (2006.01) |
| C08B 13/00 | (2006.01) |
| C08B 9/00 | (2006.01) |
| C08B 31/00 | (2006.01) |
| C08B 33/00 | (2006.01) |
| C08B 30/18 | (2006.01) |
| C08B 37/16 | (2006.01) |
| C08B 35/00 | (2006.01) |
| C08L 5/16 | (2006.01) |
| A23L 29/30 | (2016.01) |
| A23L 27/00 | (2016.01) |
| A23L 33/10 | (2016.01) |
| A23L 33/20 | (2016.01) |

(52) U.S. Cl.
CPC .......... *C08L 5/16* (2013.01); *A23L 27/75* (2016.08); *A23L 29/35* (2016.08); *A23L 33/10* (2016.08); *A23L 33/20* (2016.08); *C08B 37/0015* (2013.01); *A23V 2002/00* (2013.01)

(58) Field of Classification Search
CPC ........ A23L 1/095; A23L 1/22033; A23L 1/30; A23L 1/307; C08B 37/0015; C08L 5/16; A23V 2002/00; A23V 2250/5114; A23V 2200/332; A23V 3350/0612; A23V 2250/0644; A23V 2250/306

See application file for complete search history.

(56) References Cited

U.S. PATENT DOCUMENTS

| | | | |
|---|---|---|---|
| 5,376,645 A | 12/1994 | Stella et al. | |
| 5,523,111 A | 6/1996 | Nickel et al. | |
| 5,532,009 A | 7/1996 | Fortier | |
| 5,824,354 A | 10/1998 | Ritter et al. | |
| 6,129,945 A | 10/2000 | Awad et al. | |
| 6,254,851 B1 * | 7/2001 | Kohno et al. | 424/1.81 |
| 6,664,244 B1 | 12/2003 | Furuse et al. | |
| 6,890,549 B2 | 5/2005 | Artiss et al. | |
| 6,905,668 B1 * | 6/2005 | Kohno et al. | 424/1.81 |
| 7,105,195 B2 | 9/2006 | Plank et al. | |
| 7,547,459 B2 | 6/2009 | Plank et al. | |
| 7,569,208 B2 * | 8/2009 | Kohno et al. | 424/1.81 |
| 7,807,198 B2 | 10/2010 | Pun et al. | |
| 8,017,147 B2 * | 9/2011 | Mazed et al. | 424/450 |
| 2002/0006450 A1 | 1/2002 | Nakahara et al. | |
| 2003/0190402 A1 | 10/2003 | McBride | |
| 2004/0076690 A1 | 4/2004 | Ikemoto et al. | |
| 2004/0116382 A1 | 6/2004 | Plank et al. | |
| 2004/0161526 A1 | 8/2004 | Schmid et al. | |
| 2004/0180125 A1 | 9/2004 | Plank et al. | |
| 2004/0204502 A1 | 10/2004 | Dasseuex et al. | |
| 2005/0019475 A1 | 1/2005 | Plank et al. | |
| 2005/0215523 A1 | 9/2005 | Lai et al. | |
| 2006/0019021 A1 | 1/2006 | Plank et al. | |
| 2009/0023682 A1 | 1/2009 | Artiss et al. | |
| 2009/0029020 A1 | 1/2009 | Strassburger | |
| 2009/0185985 A1 | 7/2009 | Strassburger | |
| 2009/0214446 A1 | 8/2009 | Strassburger | |
| 2009/0227690 A1 | 9/2009 | Strassburger et al. | |
| 2009/0252854 A1 | 10/2009 | Plank | |
| 2010/0160623 A1 | 6/2010 | Strassburger | |

FOREIGN PATENT DOCUMENTS

| | | |
|---|---|---|
| CN | 1190333 A | 8/1998 |
| EP | 1 120 046 A1 | 8/2001 |
| EP | 1 477 072 A1 | 11/2004 |

(Continued)

OTHER PUBLICATIONS (R) Kim et al., "β-Cyclodextrin Reduced Obesity in C57BL/6J Mice Induced by High Fat Diet," Food Science and Biotechnology, 17(4), 700-704 (Aug. 2, 2008).*

Amber Vyas, "Cyclodextrin based novel drug delivery systems", Journal of Inclusion Phenomena and Macrocyclic Chemistry, May 23, 2008, pp. 23-42.

Joseph D. Artiss et al., "The effects of a new soluble dietary fiber on weight gain and selected blood parameters in rats", Metabolism Clinical and Experimental 55, Feb. 1, 2006, pp. 195-202.

International Search Report and Written Opinion from corresponding PCT Patent Application No. PCT/IB2011,001148, European Patent Office, Sep. 20, 2011, 13 pgs.

Australian Intellectual Property Office, "Patent Examination Report No. 1" in connection with related Australian Patent Application No. 2011228758, 3 pgs., dated Mar. 8, 2013.

(Continued)

*Primary Examiner* — Lawrence E Crane

(74) *Attorney, Agent, or Firm* — Kolisch Hartwell, P.C.

(57) ABSTRACT

A fat-binding composition contains an inclusion complex with a host molecule and a guest molecule. The guest molecule includes one or more amino acids, vitamins, flavorants or related compounds, rutin, betanin, derivatives thereof, and mixtures thereof. The fat-binding composition may be in the form of a tablet or powder, for example, and may be incorporated into a food or beverage product. If in the form of a powder or tablet, the composition may optionally contain a carbonation-forming component and may be dissolved in carbonated or non-carbonated water. The fat-binding composition may also be employed in a method for binding fat ingested by an animal which includes having the animal ingest the composition, or a food or beverage product containing the same.

15 Claims, 2 Drawing Sheets

(56) References Cited

FOREIGN PATENT DOCUMENTS

| | | |
|---|---|---|
| JP | 57177671 A | 11/1982 |
| JP | 59232054 A | 12/1984 |
| JP | 62011072 A | 1/1987 |
| JP | 04049239 A | 2/1992 |
| JP | 2002348276 A | 4/2002 |
| JP | 2008546386 A | 12/2008 |
| JP | 2009050168 A | 3/2009 |
| WO | 2004/016101 A3 | 2/2004 |
| WO | 2006/137958 A1 | 12/2006 |
| WO | 2006/137959 | 12/2006 |

OTHER PUBLICATIONS

State Intellectual Property Office of the People's Republic of China, "First Office Action" in connection with related Chinese Patent Application No. 201180023896.X, dated May 14, 2013, 30 pages.
European Patent Office, International Preliminary Report on Patentability, Jun. 20, 2012, 8 pgs., PCT/IB2011/001148, Steigler, P.
Commissioner of Patents, Trade Marks and Designs, New Zealand Intellectual Property Office, "First Examination Report" in connection with related New Zealand Patent Application No. 603003, dated Apr. 29, 2013, 2 pages.
Canadian Intellectual Property Office, Office Action in connection with related Canadian Patent Application No. 2,792,733, dated Jan. 22, 2014, 2 pages.
Otto Funk et al., "Composition and Properties of Freeze-Dried Products of Nicotinic Acid with β-Cyclodextrin and Heptakis (2,6-0-dimethyl)-β-cyclodextrin", Journal of Inclusion Phenomena and Molecular Recognition in Chemistry vol. 16, pp. 299-314, 1993.
Japanese Patent Office, "Notice of Reasons for Rejection" in connection with related Japanese App. No. 2012-557627, dated Dec. 3, 2013, 6 pages.
State Intellectual Property Office of the People's Republic of China, "Second Office Action" in connection with related Chinese Patent App. No. 201180023896X, dated Dec. 16, 2013, 10 pages.
Australian Government—IP Australia, "Patent Examination Report No. 1", in connection with related Australian Patent Application No. 2014268274, dated Apr. 14, 2015, 3 pages.
European Patent Office, "Extended European Search Report" in connection with related European Divisional Patent Application No. 14198146.4, dated Aug. 11, 2015, 11 pages.

* cited by examiner

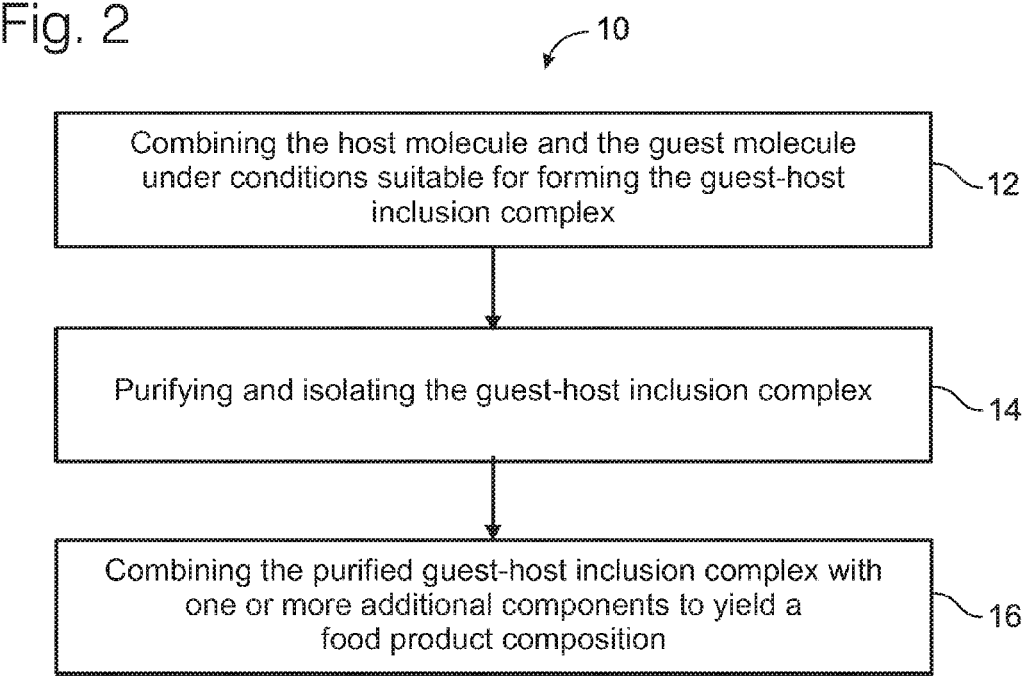
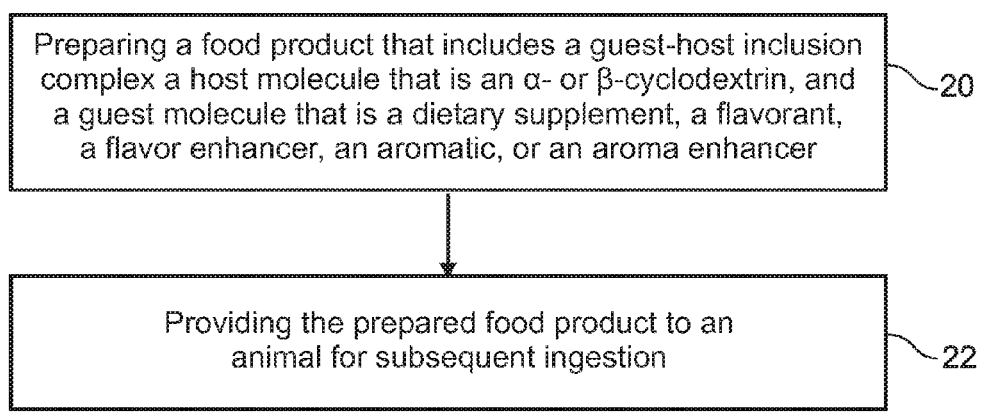

FAT-BINDING COMPOSITIONS

CROSS-REFERENCE TO RELATED APPLICATIONS

This application claims the benefit under 35 U.S.C. §119(e) of U.S. Provisional Patent application Ser. No. 61/313,734, filed Mar. 13, 2010, and entitled FAT-BINDING COMPOSITIONS, which is incorporated herein by reference for any and all purposes.

BACKGROUND

An inclusion complex is a chemical complex formed between two or more compounds, where a first compound (also referred to as a host) has a structure that defines a space into which a molecule of a second compound (also referred to as a guest) fits and non-covalently associates with the first compound. The resulting guest-host complex may be referred to as an inclusion compound, an adduct, or a host molecule. The host molecule may bind the guest molecule reversibly or irreversibly.

Cyclodextrins are host molecules that can form inclusion complexes with a variety of different guest compounds. Cyclodextrins are carbohydrates that may be prepared from hydrolyzed starch by the action of cyclodextrin-glycosyl transferase, an enzyme obtainable from several organisms such as *Bacillus macerans* or related *Bacillus* strains. Cyclodextrins have a cyclic malto-oligosaccharide structure with 6 or more alpha-1,4-linked glucose units. The most common cyclodextrins are alpha-cyclodextrin, beta-cyclodextrin, and gamma-cyclodextrin with 6, 7, and 8 linked glucose units, respectively. Under aqueous conditions, cyclodextrins can be topologically represented as toroids (as schematically shown below for gamma-cyclodextrin), with the secondary hydroxyl groups of the smaller opening, and the primary hydroxyl groups of the larger opening, exposed to the surrounding solvent. Because of this topology, the interior of the toroid, while not hydrophobic, is considerably less hydrophilic than the surrounding aqueous environment, and thus is able to host (i.e. bind) hydrophobic molecules such as fats and fatty acids. In contrast, the exterior is sufficiently hydrophilic to impart to cyclodextrins (and their inclusion complexes) substantial water solubility.

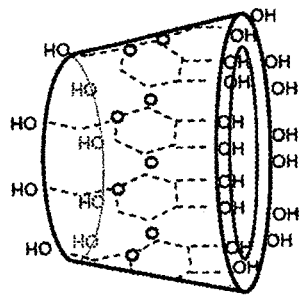

Amyloses are also host molecules that can similarly form inclusion complexes with guest compounds. Amylose is one of the two components of starch (the other being amylopectin), and may include several hundred to thousands of glucose subunits. Amylose molecules tend to form helices, with six glucose subunits constituting one complete helical sub-unit. Similar to cyclodextrins, amylose binds fatty acids to form inclusion complexes.

SUMMARY

An ingestible beverage or other food product containing one or more host molecules capable of binding fatty molecules, such as cyclodextrin and/or amylose, permit the host molecule(s) to be delivered to the gastrointestinal tract of animals prior to forming an inclusion complex with a fatty molecule, so that the host can then tightly bind neutral fat molecules in the animal's gastrointestinal tract.

It would be desirable to utilize a preformed guest-host complex that includes a weakly associated guest molecule, so that the guest molecule could be replaced and/or displaced by a fatty molecule. In particular, where the weakly associated guest molecule has nutritional or health benefits, or can enhance the flavor and/or aroma of the resulting food product, the food product can serve as a delivery mechanism for the guest molecule as well as providing a host for binding fat molecules, thereby offering a multitude of advantageous properties.

BRIEF DESCRIPTION OF THE DRAWING

FIG. 2 is a flowchart illustrating a method for preparing a food product composition according a selected embodiment of the present invention.

FIG. 3 is a flowchart illustrating a method reducing fat absorbed by an animal's digestive tract, according to a selected embodiment of the invention.

DETAILED DESCRIPTION

Figure 1:
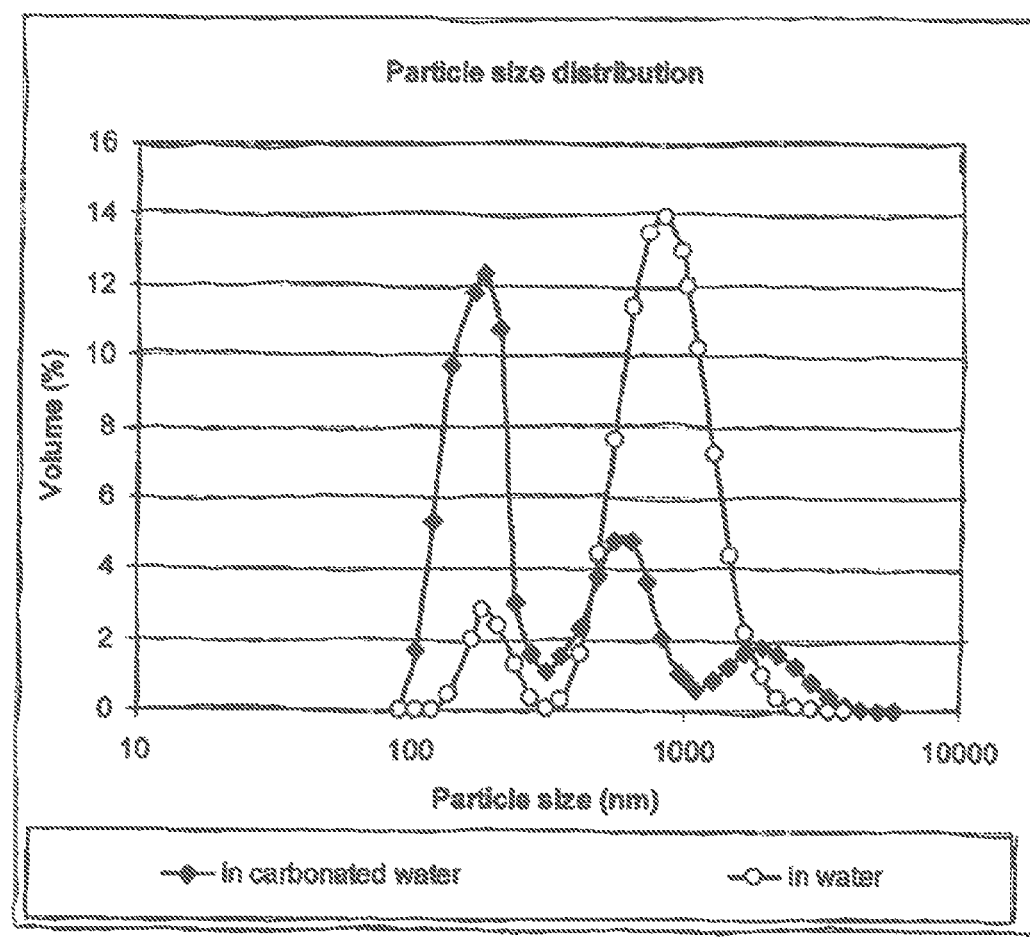
FIG. 1 illustrates the degree of aggregation of alpha-cyclodextrin dissolved in non-carbonated water and carbonated water.

The present disclosure provides examples of fat-binding compositions that include an inclusion complex formed between a guest molecule and a host molecule component.

The fat-binding compositions may take the form of a food product composition, where the food product includes a guest-host inclusion complex of a host molecule that is an α- or β-cyclodextrin, and a guest molecule that is a dietary supplement, a flavor enhancer, or aroma enhancer. Upon consumption of the food product, provided that the guest molecule is weakly and reversibly associated with the host molecule, the guest molecule is replaced under physiological conditions by a fatty molecule that is then substantially irreversibly bound to the host molecule.

The food product composition may include a mixture for preparation of a beverage. Such a beverage composition may include a guest-host inclusion complex of a host molecule that is an α- or β-cyclodextrin, and a guest molecule that is a dietary supplement, a flavor enhancer, or aroma enhancer. Again, the nature of the guest and host are selected so that the guest molecule is weakly and reversibly associated with the host molecule, and under physiological conditions after consumption, the guest molecule is replaced by a fatty molecule that is then substantially irreversibly bound.

Food product compositions such as are described above may be prepared according to a method, such as is illustrated in flowchart 10 of FIG. 2. The exemplary method includes a) combining the host molecule and the guest molecule under conditions suitable for forming the guest-host inclusion complex, at 12; b) purifying and isolating the guest-host inclusion complex, at 14; and c) combining the purified guest-host inclusion complex with one or more additional components to yield a food product composition, at 16.

The food product compositions of the present disclosure have substantially utility for preventing dietary fat from being absorbed by the consumer's digestive tract, and lend themselves to a method of reducing absorbed fat. An exemplary method for preventing dietary fat from being absorbed is illustrated in flowchart 18 of FIG. 3, where the exemplary method includes: a) preparing a food product that includes a guest-host inclusion complex of a host molecule that is an α- or β-cyclodextrin, and a guest molecule that is a dietary supplement, a flavor enhancer, or aroma enhancer, at 20; wherein the host molecule and guest molecule are selected such that within the animal's digestive tract the guest molecule will be substantially released from the host molecule, and the host molecule will form a second guest-host inclusion complex with a fatty molecule present in the digestive tract; and b) providing the prepared food product to an animal for subsequent ingestion, at 22; where the ingestion of the food product results in the fatty molecule being substantially irreversibly bound to the host molecule, and thereby removed from the digestive tract.

Of particular utility are food product compositions and beverage mixes as disclosed herein that include a guest-host inclusion complex of a host molecule and a guest molecule, where the host molecule is an α- or β-cyclodextrin, and the guest molecule is a dietary supplement, a flavorant, a flavor enhancer, an aromatic, or an aroma enhancer. In particular, these complexes may be prepared so that the binding constant of the guest-host inclusion complex is about 10-100 $M^{-1}$; and the binding constant of the complex of the same host molecule and a fatty acid is about 500-5,000 $M^1$.

As discussed herein, host molecules are compounds that tightly bind fatty molecules under physiological conditions. Examples of suitable host molecules include cyclodextrin and/or amylose molecules. The host molecule of the inclusion complex acts as a host to the guest molecule, which associates with and at least partly within the host molecule. The guest molecule may dissociate from the host molecule when the inclusion complex is in an aqueous environment, such as under physiological conditions.

Examples of products and methods of using products containing host molecules that tightly bind fatty molecules are described in: U.S. Pat. Nos. 6,890,549, 7,105,195, 7,166,575, 7,423,027, and 7,547,459; U.S. Patent Application Publication Nos. 2004/0161526, 2007/0116837, 2008/0299166, and 2009/0023682; Japanese Patent Application JP 60-094912; Suzuki and Sato, "Nutritional significance of cyclodextrins: indigestibility and hypolipemic effect of α-cyclodextrin" J. Nutr. Sci. Vitaminol. (Tokyo 1985; 31:209-223); and Szejtli et al., *Staerke/Starch*, 27(11), 1975, pp. 368-376, the complete disclosures of each of which are hereby incorporated by reference for all purposes.

The guest molecule is typically only weakly associated with the host molecule, and may also be referred to as a weak complex-forming agent. Upon ingestion by an animal, the guest molecule may dissociate from the host molecule, thereby leaving a free (i.e., uncomplexed) host molecule that is available to bind to fat molecules and related chemical entities other than the guest molecule in the animal's gastrointestinal tract.

The fat-binding compositions disclosed herein optionally may contain other components, such as one or more flavoring components, carbonation forming components (for use in forming beverage products), and/or additional nutritional or flavor enhancing components, that may or may not contain fat or fat-derived components. The host molecule may include any suitable host molecule including, but not limited to, an amylose (e.g., an acetylated amylose), alpha-cyclodextrin, beta-cyclodextrin, gamma-cyclodextrin, a derivative of a cyclodextrin, or any desired mixture of amyloses, cyclodextrins or cyclodextrin derivatives.

The guest molecule may include amino acids, vitamins, flavorants, some glycosides, N-alkyl-hydroxylamines, flavor- and aroma enhancers or any other suitable compound that forms a weak complex with the host molecule. The resulting weak complex allows the host molecule to dissociate from it and complex selectively with a fat or fat-derived chemical before, during, or after ingestion of the food product, as desired. The present disclosure also provides methods for making beverages and food products that contain these inclusion complexes.

The fat-binding compositions disclosed herein may be provided in any of a variety of forms. Some fat-binding compositions may be in the form of, or incorporated into, a solid powder, tablet, capsule, caplet, granule, pellet, wafer, powder, instant drink powder, effervescent powder, or effervescent tablet. Some fat-binding compositions may be in the form of or incorporated into aqueous beverages or other food products. These fat-binding compositions may incorporate inclusion complexes that will remain reasonably stable during storage, so that the host molecule does not dissociate from the guest molecule and form a stronger complex with a hydrophobic compound, such as a fat or fatty acid, prior to ingestion by an animal. If the host molecule were to form a complex with a hydrophobic compound prior to ingestion, then the ability of the host molecule to bind fats within the gastrointestinal tract might be compromised, thereby reducing its beneficial properties. For example, some hydrophobic compounds, such as fats or fatty acids, may be selectively and specifically excluded from the fat-binding composition.

Alternatively, the fat-binding composition may include small amounts of such hydrophobic compounds, or may include an inclusion complex that either is physically separated from such hydrophobic compounds, or is selected so as not to bind to any such hydrophobic compound present in the fat-binding composition.

Non-limiting examples of fat-binding compositions include farinaceous food products, that is food products that contain starches derived from cereal grains or starchy roots. Farinaceous food products may include nutrition bars, snack bars, breakfast cereals, pancakes, waffles, muffins, fruit filled pastries, tortillas, corn chips, tortilla chips, snack crackers, breads, cakes, cookies, pies, etc. Non-limiting examples of fat-binding compositions in the form of non-farinaceous food products may include french fries, tempura, veggie burgers, refried beans, hummus, tahini, potato chips, dairy products (e.g., milk, cream, pudding, butter, ice cream, cheese, processed cheese products, yogurt, yogurt products, etc.), egg products, and meat products (e.g. prepared beef, lamb, pork, poultry, seafood products, frankfurters, deli slices, sausages, fish sticks, chicken fingers, etc.). The fat-binding compositions also may be in the form of confectionery products, including but not limited to chewing gum, chocolate, and hard candies such as lollipops, breath mints, or after-dinner mints. The fat-binding compositions also may be in the form of condiments, including but not limited to gravies, sauces, salad dressings, mayonnaise, etc. All of the above examples of food products selectively may contain fat, or selectively may be low fat or non-fat.

The present disclosure also provides methods for binding fats ingested by an animal, such as a human. For example, some methods may include (a) preparing a beverage by dissolving an inclusion complex formed by a guest molecule complexed with a host molecule capable of dissociating from the guest molecule and forming an inclusion complex with a nearby hydrophobic molecule, such as a fatty molecules, under physiological conditions, and (b) having the animal orally ingest the beverage, whereupon the host molecule dissociates from the guest molecule and tightly binds to a nearby hydrophobic molecule, such as a fat or fat derivatives, before the fat or fat derivative is absorbed in the gastrointestinal tract of the animal. The guest molecule may include one or more amino acids, vitamins, flavorants, glycosides, or N-alkyl-hydroxylamines, provided that they exhibit the requisite binding affinities to have utility as guest molecules as described in the present disclosure.

1. The Host Molecule

The host molecule may include any suitable molecule that is capable of (a) binding a guest molecule to form a first inclusion complex, (b) readily dissociating from the guest molecule under physiological conditions, and (c) tightly binding a hydrophobic molecule to form a second inclusion complex with a nearby hydrophobic molecule under physiological conditions. Non-inclusive examples of host molecules may include amyloses, amylose derivatives, cyclodextrins (including, but not limited to, alpha-cyclodextrin, beta-cyclodextrin, and gamma-cyclodextrin), cyclodextrin derivatives, or any desired mixture of amyloses, cyclodextrins or cyclodextrin derivatives. It has been determined that alpha-cyclodextrin and beta-cyclodextrin possess particular utility as host molecules according to the present disclosure.

If the host molecule is in the form of an amylose component, the amylose component may contain glucose units expressed as degree of polymerization (DP) in the range of DP=10-900, and more preferably DP=20-200, and most preferably DP=30-80. Amylose derivatives may include, but are not limited to, acetylated amyloses. The amylose component preferably may have a structure that includes alpha-1,4-glycosidic linkage bound D-glucopyranoses in a helical arrangement that defines a central cavity for binding hydrophobic molecules, such as fatty molecules. For example, the A- and B-starch helix of V-amylose may include a parallel, left-handed double helix defining a central cavity. The helices of amylose inclusion complexes may be stabilized by the hydrophobic forces created by the host-guest interactions, intermolecular hydrogen bonds between glucoses in adjacent amyloses, and intramolecular hydrogen bonds formed by adjacent turns of the helix. See Hinrichs, W., et al., "An Amylose Antiparallel Double Helix at Atomic Resolution," *Science*, (1987), 238(4824): 205-208, the complete disclosure of which is hereby incorporated by reference for all purposes. An amylose host molecule maybe used to form fat-binding compositions, where the desired guest molecule has low molecular weight and is generally more hydrophobic. For example, an amylose host molecule may be used to form an inclusion complex with a guest molecule having a low molecular weight, while being more hydrophilic, such as the non-limiting examples of flavorants, colorants, vitamins, amino acids, and/or amines.

Fat-binding compositions containing amylose host molecules may include various concentrations of amylose component, depending on the form of the fat-binding composition. If the fat-binding composition containing an amylose host molecule is in solid form, the amylose component preferably may be present in a concentration range of about 10-90% w/w, or about 15-70% w/w, or about 15-60% w/w. More preferably, the amylose component may be present in a concentration range of about 10-50% w/w, or about 15-40% w/w. Most preferably, the amylose component may be present in a concentration range of about 20-25% w/w. If the fat-binding composition containing the amylose host molecule is in the form of an aqueous beverage, the amylose component preferably may be present in a concentration range of about 0.1-75% w/v, or about 1-50% w/v, or about 1-25% w/v. More preferably, the cyclodextrin component may be present in a concentration range of about 1-10% w/v. Most preferably, the cyclodextrin component may be present in a concentration range of 5-8% w/v.

If the host molecule is in the form of a cyclodextrin component, then the cyclodextrin may be selected based upon its desired binding properties with selected guest molecules and with target hydrophobic molecules. Non-limiting examples of acceptable cyclodextrins may include commercially available and government regulatory approved forms of alpha-, beta- and gamma-cyclodextrins which are composed of six, seven or eight glucose units linked by $\alpha$-(1,4)-glycosidic bonds in a toroidal structure having a cavity. The number of glucose units determines the internal dimensions of the cavity and its volume. The cyclodextrin compounds are typically capable of complex-forming with various hydrophobic molecules so as to encompass the molecule, or a part thereof, within the cyclodextrin cavity, and thereby influence the physicochemical properties of the complexed guest molecule. The cyclodextrin component may be selected so as to form a first inclusion complex with a selected guest molecule and, after dissociation with the agent (such as in an aqueous environment), to form a second inclusion complex with other target hydrophobic molecules, such as fat or fat-derived molecules. Other desired properties of the cyclodextrin component may include forming water-insoluble highly aggregated forms of inclusion complexes with fatty acids and other lipids under physiological conditions in order to achieve fat immobilization.

Generally, narrow cavity cyclodextrins, such as alpha- and beta-cyclodextrins, are the most effective cyclodextrins for forming complexes with, and immobilizing, linear fatty acids and glycerides. Although gamma-cyclodextrin may be less effective for forming complexes with and immobilizing saturated fatty acids, gamma-cyclodextrin does complex well with unsaturated fatty acids (i.e., fatty acids having two, three or more double bonds in the fatty acid molecule). As used herein, complex formation refers to a reversible non-covalent interaction between cyclodextrins and the guest molecule(s), a dimensional fit between the cyclodextrin cavity and the guest molecule(s). The lipophilic cavity of cyclodextrin molecules provides a microenvironment for a hydrophobic geometrically-compatible organic molecule and forms a stable, protective supramolecular system referred to herein as an inclusion complex. No covalent bonds are broken or formed during formation of an inclusion complex.

The main driving force of complex formation is considered to be the release of enthalpy with the displacement of water molecules from the cyclodextrin cavity. Water molecules are displaced by the more hydrophobic guest molecules present in solution to attain an apolar-apolar association and a decrease in the cyclodextrin ring strain resulting in more stable, lower energy state compounds due to this molecular complexation. For complex formation, there must be a favorable net energy driving force that pulls the guest molecule into the cyclodextrin cavity. The complexation of the guest molecule within the host molecule is a dynamic process in solution. The binding constant is a significant parameter in determining how well the host-guests complex fits together and the extent of specific local molecular interactions, such as hydrogen bonding, hydrophobic interactions, etc.

In some embodiments, the selected cyclodextrin component may be composed mainly of alpha-cyclodextrin, or an alpha-cyclodextrin derivative, in view of its geometric suitability for forming stable inclusion complexes with linear fatty acids, as well as mono- and di-glycerides. Advantageously, alpha-cyclodextrins generally form insoluble complexes with fatty acids and glycerides.

If the fat-binding composition is in solid form, the cyclodextrin component may be present in a concentration range of about 10-90% w/w, or about 15-70% w/w, or about 15-60% w/w. Preferably, the cyclodextrin component may be present in a concentration range of about 10-50% w/w, or about 15-40% w/w. More preferably, the cyclodextrin component may be present in a concentration range of about 20-25% w/w.

If the fat-binding composition is in the form of an aqueous beverage, the cyclodextrin component may be present in a concentration range of about 0.1-75% w/v, or about 1-50% w/v, or about 1-25% w/v. Preferably, the cyclodextrin component may be present in a concentration range of about 1-10% w/v. More preferably, the cyclodextrin component may be present in a concentration range of 5-8% w/v.

Cyclodextrin derivatives may include alkylated, hydroxyalkylated, alkoxyalkylated, acetylated, quaternary ammonium salts, carboxyalkylated, maltosylated, and glucosylated derivatives. Alkyl groups of cyclodextrin derivatives may be straight chain or branched, may have main chain lengths of one to three carbons, and may have a total of one to six, and preferably one to three carbon atoms. Some non-limiting examples of cyclodextrin derivatives may include methylated beta-cyclodextrins, 2-hydroxypropylated beta-cyclodextrins, water soluble beta-cyclodextrin polymers, partially acetylated alpha-, beta-, and/or gamma cyclodextrins, ethylated alpha-, beta-, and/or gamma-cyclodextrins, carboxyalkylated beta-cyclodextrins, quaternary ammonium salts of alpha-, beta-, and/or gamma-cyclodextrins, branched (glucosylated-maltosylated) alpha-, beta-, and gamma cyclodextrins, as well as mixtures of any combination of these derivatives, together or in combination with one or more cyclodextrins. An exemplary mixture of cyclodextrins may include a combination of alpha-, beta- and gamma-cyclodextrin in a weight ratio range of about 1:1:1 to 2:2:1, respectively. The cyclodextrin may be in a hydrate crystalline and/or amorphous form, including but not limited to the hydrate and/or amorphous forms of alpha-cyclodextrin, beta-cyclodextrin, gamma-cyclodextrin, and mixtures thereof.

As discussed above, host molecules may, in part, be selected based on their affinity for target molecules, such as hydrophobic molecules, that are located in a target environment, such as in the gastrointestinal tract of an animal, and that would be desirable to bind and immobilize those molecules so that they exit the animal's body as solid waste. Host molecules selected for such a purpose preferably may have minimum binding constants for the target compound in the range of about 500-5,000 $M^{-1}$, more specifically in the range of about 600-1,000 $M^{-1}$, and preferably about 800 $M^{-1}$ or higher within those ranges.

II. The Guest Molecule

The guest molecule may be selected to form an inclusion complex with a selected host molecule, where the binding constant for the inclusion complex is relatively low. The guest molecule may bind to the host molecule as a guest molecule in the cavity of the host molecule, and/or may form a so-called outer sphere complex, where the selected guest molecule binds to the host molecule at a position at or around the rim(s) of the host molecule cavity. For example, the selected guest molecule may be bound to a cyclodextrin molecule at or around the primary and/or secondary hydroxyl groups at the rims of the cyclodextrin torus. The guest molecule may be selected so that it binds to the selected host molecule with a binding constant in the range of about 10 to 800 $M^{-1}$, preferably 30 to 150 $M^{-1}$, and more preferably 40 to 100 $M^{-1}$. The guest molecule thereby may act as a placeholder in the cavity of the host molecule, and may have the capability of dissociating therefrom, especially in an aqueous environment, in order to allow the cyclodextrin to bind with fat and fat-derived components before, during, and/or after ingestion, as desired. In addition, some guest molecules that form an outer sphere complex with the selected cyclodextrin may reduce or prevent self-aggregation of dissolved, hydrated cyclodextrin molecules by destroying intermolecular hydrogen bonds that form between two neighboring cyclodextrin molecules in water.

In a particular embodiment of the invention, the binding constant of the guest-host inclusion complex is about 10-100 $M^{-1}$; and the binding constant of a complex of the host molecule and a fatty acid is about 500-5,000 $M^{-1}$.

Guest molecules may include amino acids, various vitamins, various flavorants and related compounds, various colorants and related compounds, some glycosides, and N-alkyl-hydroxylamines, as well as combinations or mixtures of these agents. These agents may weakly complex with the host molecule so as to have the capability of dissociating therefrom in order to allow the host molecule to complex with a fat or fat-derived component before, during, and/or after ingestion, as desired. Preferred guest molecules may include flavorants, flavorant related compounds, and water soluble vitamins including, but not limited to, ascorbic acid, niacin and niacinamide.

Non-limiting examples of amino acids may include aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, salts thereof, and mixtures thereof. Also included are N-alkyl $C_1$-$C_3$ and N-acylated $C_1$-$C_3$ derivatives of these amino acids, and mixtures of any of the amino acids or derivatives thereof.

Non-limiting examples of vitamins may include nicotinamide (vitamin $B_3$) and pyridoxal hydrochloride (vitamin $B_6$), ascorbic acid, edible ascorbyl esters, riboflavin, niacinamide, niacin, pyridoxine, thiamine, vitamin $B_9$, folic acid, folate, pteroyl-L-glutamic acid, pteroyl-L-glutamate, salts thereof, and mixtures thereof.

Non-limiting examples of flavorants may include apple, apricot, banana, grape, blackcurrant, raspberry, peach, pear, pineapple, plum, orange, and vanilla flavorants. Examples of flavorant related compounds include butyl acetate, butyl isovalerate, allyl butyrate, amyl valerate, ethyl acetate, ethyl valerate, amyl acetate, maltol, isoamyl acetate, ethyl maltol, isomaltol, diacetyl, ethyl propionate, methyl anthranilate, methyl butyrate, pentyl butyrate, and pentyl pentanoate.

Non-limiting examples of flavor and taste enhancers may include maltol, ethylated-maltol, disodium-inosinate-5'-monophosphate, sodium, and/or potassium 5' guanylate, sodium and/or potassium-glutamate, L-leucine.

Regarding appropriate flavorants and related compounds, it is noted that Example 9 below provides the results of measurements of the apparent binding constants for several tested compounds. These binding constants appear to be generally appropriate for indicating the formation of weak complexes with selected cyclodextrins. Thus, it is possible for these tested compounds to serve both the purpose of a flavor component and a guest molecule, although other compounds also may serve both of these purposes. In this regard, a flavorant may be selected so that it weakly binds to a selected cyclodextrin component with a binding constant in the range of about 10 to 800 $M^{-1}$, preferably 30 to 150 $M^{-1}$, and more preferably 40 to 100 $M^{-1}$.

Non-limiting examples of colorants may include those that are known to be more water soluble and less lipophilic. Examples of colorants with those properties are betalains, such as betacyanins and betaxanthins, including vulgaxanthin, miraxanthin, portulaxanthin and indicaxanthin; anthocyanidins, such as aurantinidin, cyanidin, delphinidin, europinidin, luteolinidin, pelargonidin, malvidin, peonidin, petunidin and rosinidin, as well as all corresponding anthocyanins (or glucosides) of these anthocyanidins; and turmeric type colorants including phenolic curcuminoids, such as curcumin, demethoxycurcumin and bisdemethoxycurcumin. Lipophilic colorants should be avoided because they will tend to prevent the desired fat-binding by forming complexes with cyclodextrins.

Non-limiting examples of glycosides may include rutin and betanin. Regarding betanin, it is noted that this is a red glycosidic food dye that can be obtained from beets. Betanin is reported to exhibit potential anti-aging properties, as well as to protect against free radicals.

N-alkyl-hydroxylamines may include compounds wherein the alkyl group has one to four carbon atoms, the following alkyl groups: methyl, ethyl, n-propyl, isopropyl, 1-methylpropyl, 2-methylpropyl, n-butyl, and t-butyl. Preferred N-alkyl-hydroxylamines include N-t-butyl-hydroxylamine and N-methyl-hydroxylamine. N-alkyl-hydroxylamines have been reported to exhibit advantageous antioxidant activity, as well as potential anti-aging effects as evidenced by the ability to delay the senescence of in vitro human cell lines. Atamna, H. et al, *J. Biol. Chem.*, Vol. 275, No. 10, pp. 6741-6748, 2000; Carney et al., (1991), *Proc. Natl. Acad. Sci. U.S.A.*, 88, pp. 3633-3636, the complete disclosures of which are hereby incorporated by reference for all purposes. Example 10 below describes the production of an N-alkyl-hydroxylamine/cyclodextrin complex having a binding constant within the preferred range discussed above.

Some non-limiting examples of guest molecules may include one or more of the following: niacin and niacin derivatives (e.g., niacinamide), vitamin $B_6$ (e.g. in the form of pyridoxamine, pyridoxal or pyridoxine), glutamic acid and salts thereof (e.g., Na-L-glutamate and L-glutamic acid), asparaginic acid (e.g. L-asparaginic acid), lysine and lysine derivatives (e.g., L-Lysine and N-methyl-L-Lysine), arginine (e.g., L-arginine and N-guanidinomethyl-L-arginine), proline (e.g., L-proline), ascorbic acid, riboflavin, alanine (e.g., L-alanine), creatine, carnitine (e.g. L-carnitine), taurine, vitamin $B_9$, folic acid, folate, betanin, rutin, apple flavorant, apricot flavorant, banana flavorant, butyl acetate, butyl isovalerate, allyl butyrate, amyl valerate, ethyl acetate, ethyl valerate, amyl acetate, and maltol. The guest molecule also may include N-alkyl $C_1$-$C_3$ and N-acylated $C_1$-$C_3$ derivatives of the aforementioned amino acids. All of the above examples of amino acids, vitamins, flavorants and related compounds, glycosides, and N-alkyl-hydroxylamines also may be in appropriate salt or hydrate forms.

Regarding taurine, in addition to being a guest molecule with alpha-, beta- and gamma-cyclodextrin, it also inhibits self-aggregation of these cyclodextrins by forming a complex with the cyclodextrins that disrupts the formation of intermolecular hydrogen bonds between adjacent cyclodextrins. Taurine also may bind to amylose host molecules to a lesser extent, thereby forming complexes with amylose having lower binding constants than complexes with taurine and alpha-, beta- or gamma-cyclodextrins. Taurine may be an effective guest molecule with other host molecules as well.

Nutritionally, taurine has been shown to prevent oxidative stress induced by exercise. In a 2008 study, taurine has been shown to reduce the secretion of apolipoprotein 8100 and lipids in HepG2 cells. Yanagita et al., "Taurine reduces the secretion of apolipoprotein 8100 and lipids in HepG2 cells, *Lipids in Health and Disease* 2008 Oct. 17; 7:38, the complete disclosure of which is hereby incorporated by reference for all purposes. High concentrations of serum lipids and apolipoprotein 6100 (an essential structural component of VLDL and LDL lipoproteins) are major risk factors associated with atherosclerosis and coronary heart disease. Hence, it is possible that taurine supplementation is beneficial for the prevention of these diseases. In a 2003 study, dietary taurine was demonstrated to have a hypocholesterolemic (blood cholesterol-lowering) effect in young overweight adults. Zhang et al., "Beneficial effects of taurine on serum lipids in overweight or obese non-diabetic subjects," *Amino Acids*, 2004 June; 26(3):267-71, the complete disclosure of which is hereby incorporated by reference for all purposes. Furthermore, Zhang et al. reported that body weight also decreased significantly in the taurine supplemented group. Taurine has also been shown to help people with congestive heart failure by increasing the force and effectiveness of heart-muscle contractions. In addition, it has been shown to be effective in removing fatty liver deposits in rats, preventing liver disease, and reducing cirrhosis in tested animals. There is also evidence that taurine is beneficial for adult human blood pressure and possibly, the alleviation of other cardiovascular ailments. For example, in patients suffering essential hypertension, taurine supplementation resulted in measurable decreases in blood pressure. Choi et al., "The effect of dietary taurine supplementation on plasma and liver lipid concentrations and free amino acid concentrations in rats fed a high-cholesterol diet," *Advances in Experimental Medicine and Biology*, 2006; 583: 235-42, the complete disclosure of which is hereby incorporated by reference for all purposes.

Regarding creatine, functionally this compound appears to be an acceptable guest molecule for alpha-, beta- and gamma-cyclodextrins and for amylose, although creatine may be used as a guest molecule for other host molecules as well. Similar to taurine, creatine inhibits the self-aggregation of cyclodextrin dissolved in water by inhibiting intermolecular hydrogen bond formation between adjacent cyclodextrin molecules. Nutritionally, researchers have concluded that diet supplementation with creatine significantly increased intelligence compared with placebo. A subsequent study found that creatine supplements improved cognitive ability in the elderly. Rae et al., 2003 "Oral creatine monohydrate supplementation improves cognitive performance; a placebo-controlled, double-blind cross-over trial," *Proceedings of the Royal Society of London—Biological Sciences*, (2003), 270 (1529): 2147-50; McMorris et al., "Creatine supplementation and cognitive performance in elderly individuals," *Aging, Neuropsychology, and Cognition*, (2007), 14: 517-528, the complete disclosures of which are hereby incorporated by reference for all purposes.

If the fat-binding composition is in solid form, the guest molecule may be present in a concentration range of about 1-50% w/w. Preferably, the guest molecule may be present in a concentration range of about 1-40% w/w or about 1-25% w/w. More preferably, the guest molecule may be present in a concentration range of about 5-15% w/w.

If the fat-binding composition is in the form of an aqueous beverage, the guest molecule may be present in a concentration range of about 0.1-25% w/v or about 1-20% w/v. Preferably, the guest molecule may be present in a concentration range of about 1-15% w/v or about 1-10% w/v or about 3-8% w/v. More preferably, the guest molecule may be present in a concentration range of about 5-8% w/v.

III. The Inclusion Complex

As noted above, the inclusion complex may include a host molecule complexed with guest molecule molecules. In the form of a solid product, such as a solid powder or tablet, the inclusion complex may exhibit some unique properties as compared to a solid composition containing essentially the same components, but without the preliminary formation of the inclusion complex. The inclusion complex is essentially a chemical entity having non-covalent hydrogen bonds formed between the host molecule and the guest molecule molecule. The inclusion complex, in its solid form, has the potential of dissociating into the host molecule for fat binding, and the guest molecule for other beneficial properties, such as nutrition or flavor, when the inclusion complex is introduced to an aqueous environment, such as upon dissolution in an aqueous beverage, or upon ingestion.

When in the form of a solid product, the host molecule and one or more types of a guest molecule may be substantially in the form of an inclusion complex, as described above. Preferably, over about 25% of the host molecule is complexed with one or more types of a guest molecule in the form of an inclusion complex. It is progressively more preferable to have over 35%, 45%, 50%, 60%, 70%, 80%, 90%, and 95% of the host molecule complexed. If the inclusion complex is dissolved in an aqueous environment, such as an aqueous beverage, or the environment within the gastrointestinal tract of an animal, the guest molecule may partly or fully dissociate from the host molecule. After dissociation, the free (i.e. uncomplexed) host molecule may then bind to adjacent hydrophobic molecules, such as fatty molecules or other related chemical entities. As discussed below, the specific host molecule and guest molecule for a particular inclusion complex may be selected based on its desired application, which may depend on the binding affinity between the host molecule and the guest molecule. In addition, the guest molecule, which may be selected to provide nutritional benefits and/or flavoring, also may be selected based on its ability to advantageously reduce or prevent self-aggregation of the dissolved host molecules, which may help to maintain the fat binding properties of the host molecule.

The host molecule and the guest molecule selected for a particular inclusion complex in part may depend on the binding affinity between the host molecule and the guest molecule under selected conditions, such as aqueous and/or physiological conditions. Binding affinities between the host molecule and guest molecule may be determined experimentally. One way to determine these binding affinities is to measure differences in the observable characteristics of the guest molecule when in the presence and absence of the host molecule. For example, the guest molecule may have an acidic dissociation constant, or pKa, that depends on the environment of the guest molecule, and that is measurably different in the presence or absence of a dissolved host molecule due to the formation of the non-covalent inclusion complexes. The measurable difference in the acidic pKa of the guest molecule may allow one to determine the binding constant exhibited by the guest/host inclusion complexes, in situ. This method of determining binding constants was originally introduced by Connors, et al. for describing binding constants of organic aromatic acids and cyclodextrins. See K. A. Connors et al., *J. Pharm. Sci.*, 65(3), pp. 379-83, 1976, the complete disclosure of which is hereby incorporated by reference for all purposes.

Another method of assessing the binding affinity between selected host molecules and selected guest molecules involves an analysis of freezing point depression properties. Specifically, the affinity between host molecules and guest molecules as guest compounds may be measured by separately determining the osmotic pressure of diluted aqueous solutions of host molecules, diluted aqueous solutions of guest molecules separately, and a solution containing both the host molecules and the guest molecule. If the measured osmotic pressure of the combination in solution is less than the sum of the osmotic pressure measurements of each component separately in solution, then the experimental data supports the conclusion that some inclusion complexes, between host molecules and guest molecules, exist in solution. This interaction (between cyclodextrin and alcohols) is addressed in Suzuki, M. et al. *Chem. Pharm. Bull.*, 36. p. 720, 1988, the complete disclosure of which is hereby incorporated by reference for all purposes.

Once the binding affinities of host molecules for selected guest molecules has been determined for selected conditions, such as physiological conditions, the known binding affinities can be used to assist with the selection of optimal host molecules and guest molecules for particular applications.

The host molecule and the guest molecule selected for a particular inclusion complex also may depend on the nutritional benefits and/or flavoring benefits afforded by the guest molecule, and based on the ability of the guest molecule to advantageously reduce or prevent self-aggregation of the selected host molecule. The nutritional and/or flavoring benefits associated with the various guest molecules are discussed above. The ability of the selected guest molecule to inhibit self-aggregation of the selected host molecule may be experimentally measurable, and may be used to assist with the selection of optimal host molecules and guest molecules for particular applications.

IV. Unacceptable Hydrophobic Compounds as Guest Molecules

A beneficial effect of the guest molecule in the fat-binding compositions disclosed herein, is that upon complexation of a host molecule with a guest molecule, the guest molecule can act as a "placeholder" in the cavity of the host molecule, so that upon dissociation therefrom in an appropriate environment, such as an aqueous environment, the cyclodextrin molecule can then selectively bind hydrophobic molecules, such as fatty molecules and related chemical entities. In addition, the presence of the guest molecule in an aqueous environment advantageously may reduce or prevent self-aggregation of cyclodextrin molecules, thereby inhibiting a decrease in the number of host molecules available for binding hydrophobic molecules. Acceptable guest molecules therefore may specifically exclude molecules that have a high binding affinity for the host molecule, such as hydrophobic molecules which do not readily dissociate from the host molecule in an aqueous environment, and/or may not reduce or prevent self aggregation of host molecules.

Hydrophobic compounds that may have high binding affinity for the host molecules, and thus may be unacceptable as guest molecules may include, but are not limited to fats, waxes, sterols, monoglycerides, diglycerides, triglycerides, phospholipids, fatty acids, fat soluble vitamins, essential oils, terpenes, and fat-soluble colorants such as carotenoids, etc. Non-limiting examples of fatty acids may include palmitic acid, stearic acid, lauric acid, myristic acid, oleic acid, and polyunsaturated fatty acids, such as alpha-omega polyunsaturated fatty acids, as well as salts and esters thereof. Additional hydrophobic compounds that may be unacceptable as guest molecules may include: fatty acids; esters of fatty acids derived from dietary fats, such as animal fats like lard and butter; vegetable fats, such as coconut oil, palm oil, wheat germ oil, cottonseed oil, soya oil, olive oil, corn oil, sunflower oil, safflower oil, hemp oil, and canola oil; etc.

In some embodiments, the fat-binding composition may be produced in solid form with an inclusion complex having a host molecule and a guest molecule, and this product then subsequently may be incorporated into a food product, such as a nutrition bar or other food product, where the food product also contains one or more of the above-noted unacceptable hydrophobic compounds. These food products, which contain unacceptable hydrophobic compounds, nonetheless may function as fat-binding compositions, as long as a substantial proportion of the inclusion complexes between the host molecule and the guest molecule remain in stable form in the food product without resulting in replacement of the guest molecule with an unacceptable hydrophobic compound before ingestion.

V. Flavor Components

Flavor components may include sugars, non-sugar sweeteners, and/or other taste improving components. Non-limiting examples of sugars may include honey, sucrose, fructose, glucose, galactose, ribose, hydrolyzed starch, and corn syrups, especially those with a dextrose equivalent of DE 42 and DE 35.

Non-limiting examples of non-sugar sweeteners may include: synthetic high potency sweeteners, such as sucralose, potassium acesulfame, aspartame, alitame, saccharin, neohesperidin dihydrochalcone, cyclamate, neotame, N—[N-[3-(3-hydroxy-4-methoxyphenyl)propyl]-L-alpha-aspartyl]-L-phenylalanine 1-methyl ester, N—[N-[3-(3-hydroxy-4-methoxyphenyl)-3-methylbutyl]-L-alpha-aspartyl]-L-phenylalanine 1-methyl ester, N—[N-[3-(3-methoxy-4-hydroxyphenyl)propyl]-L-alpha-aspartyl]-L-phenylalanine 1-methyl ester, salts thereof, and the like; and naturally occurring high potency sweeteners, such as rebaudioside A, rebaudioside B, rebaudioside C, rebaudioside D, rebaudioside E, rebaudioside F, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobtain, baiyunoside, osladin, polypodoside A, pterocaryoside A, pterocaryoside B, mukurozioside, phlomisoside I, periandrin I, abrusoside A, and cyclocarioside I.

Non-limiting examples of guest molecules that may function as flavor enhancers, or flavor enhancing agents, include polyol additives such as erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, and reduced glucose syrup.

Still further non-limiting examples of flavor components may include one or more of the above-listed flavorants and related compounds that are described as useful guest molecules. These flavorants and related compounds can serve the dual function of providing a guest molecule and providing flavor. Also, these flavorants and related compounds optionally may be combined with any of the flavor components discussed above.

Some preferred flavor components may include xylitol, fructose, sorbitol, high fructose syrup, and corn syrup in the form of low dextrose equivalent (DE) corn syrup.

If the fat-binding composition is in solid form, the flavor component may be present in a general concentration range of about 1-40% w/w, or about 1-25% w/w. Preferably, the flavor component may be present in a concentration range of about 2-10% w/w. More preferably, the flavor component may be present in a concentration range of about 3-5% w/w. In addition, it is noted that if the flavor component includes a significant amount of a high potency sweetener, the amount of this type of sweetener present in the fat-binding composition may be lower than 1% w/w, and may be present in an amount of about 0.1% w/w or lower if acceptable sweetening properties are exhibited.

If the fat-binding composition is in the form of an aqueous beverage, the flavor component may be present in a concentration range of about 1-25% w/v, or about 1-15% w/v. Preferably, the flavor component may be present in a concentration range of about 1-10% w/v, or about 1-5% w/v. In addition, if a high potency sweetener is used, the concentration may be lower than 1% w/v, and may be present in the range of an amount of about 0.01-0.1% w/v or lower if acceptable sweetening properties are exhibited.

VI. Carbonation-Forming Components

Some fat-binding compositions may include carbonation-forming components that produce carbonation, or effervescence, upon dissolution of the fat-binding composition into an aqueous environment. As discussed below, carbonation-forming components advantageously may inhibit self-aggregation of dissolved host molecules, thereby increasing the number of host molecules available for binding hydrophobic molecules.

It has been experimentally shown that alpha-cyclodextrin exhibits less aggregation in carbonated water than in non-carbonated water. Aqueous solutions of alpha-cyclodextrin (2% w/v) dissolved in normal tap water and carbonated water (an effervescent mimic), were prepared under identical conditions. These solutions were then subjected to laser light scattering to determine the distribution of particle sizes in each solution. FIG. 1 shows a comparison between the particle size distributions of alpha-cyclodextrin dissolved in non-carbonated water (shown in open circles) and carbonated water (shown in filled diamonds). As can be seen from FIG. 1, the majority of cyclodextrin particles in non-carbonated tap water have a size of about one micron (1,000 nm, as shown by the rightmost peak), while cyclodextrin particles in carbonated water have a significantly smaller size of generally less than 0.5 microns (500 nm, as shown by the leftmost peak). This experiment shows that the aggregation of cyclodextrin molecules is significantly reduced in carbonated water as compared to non-carbonated water. Cyclodextrin molecules in a less aggregated form likely include more available binding sites for complex formation. This experiment thus provides evidence that is consistent with the conclusion that carbonation allows for the availability of more cyclodextrin binding sites for forming complexes with fats. Moreover, fat-binding compositions that include carbonation-forming compounds may be more effective for binding fats due to the carbonation's effect of inhibiting aggregation.

With respect to the binding of fats by the above compositions, there are two factors that increase the effectiveness of preventing ingestion of the target hydrophobic molecules (fat molecules) by the animal. First, there is the desired relatively high binding constant that indicates the tight and strong bond between the host and the fat molecule. Second, there is the desired encapsulation of the fat molecule by one or more of the host molecules. In the case of cyclodextrin host molecules, it is desirable to have two or three host molecules bind to a fat molecule to more completely encapsulate it. The fat molecule will typically be relative long compared to the cyclodextrin, and that is why having two or three cyclodextrins bind to a single fat molecule is desirable. By increasing the encapsulation of the fat molecule, there is a greater likelihood that the fat molecule will not be absorbed into the animal's gastro-intestinal tract, and will therefore exit the animal's body as a microcrystalline or amorphous solid in the animal's solid waste.

Non-limiting examples of carbonation-forming components may include sodium carbonate, sodium bicarbonate, potassium carbonate and potassium bicarbonate. Preferred carbonation-forming components may include sodium carbonate, and sodium bicarbonate.

If the fat-binding composition is in solid form, the carbonation-forming component may be present in a concentration range of about 1-60% w/w or about 5-60% w/w. Preferably, the carbonation-forming component may be present in a concentration range of about 5-45% w/w or 10-45% w/w. More preferably, the carbonation-forming component may be present in a concentration range of about 10-15% w/w.

If the fat-binding composition is in the form of an aqueous beverage, the carbonation-forming component may be present in a concentration range of about 1-30% w/v or about 1-25% w/v. Preferably, the carbonation-forming component may be present in a concentration range of about 2-15% w/v or 2-10% w/v. More preferably, the carbonation-forming component may be present in a concentration range of about 2-5% w/v.

VII. Other Components

Some fat-binding composition may include yet other components that affect the taste and/or nutritional value of the composition. These additional components may include, but are not limited to, one or more of the following: flavor additives, nutritional ingredients and/or various hydroxyl-acids that act as host molecule aggregation-preventing additives in the formulations. Non-limiting examples of such other components may include citric acid, ascorbic acid, sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, maltodextrin, mono-, di-, tri-basic sodium or potassium salts of phosphoric acid (e.g., inorganic phosphates), salts of hydrochloric acid (e.g., inorganic chlorides), sodium bisulfate. Non-limiting examples of hydroxyl-acids that prevent cyclodextrin aggregation may include isocitric acid, citric acid, tartaric acid, malic acid, threonic acid, salts thereof and mixtures thereof. These hydroxyl-acids also may exhibit some nutritional benefits. Other non-limiting examples of additional optional components, such as taste additives, that may be used include suitable organic salts, such as choline chloride, alginic acid sodium salt (sodium alginate), glucoheptonic acid sodium salt, gluconic acid sodium salt (sodium gluconate), gluconic acid potassium salt (potassium gluconate), guanidine HCl, glucosamine HCl, amiloride HCl, monosodium glutamate (MSG), adenosine monophosphate salt, magnesium gluconate, potassium tartrate (monohydrate), and sodium tartrate (dihydrate).

Another component that may be included in some fat-binding compositions is a lipase. Animal lipases are used conventionally in digestive pharmaceutical products. Non-limiting examples of lipases may include pancreatic lipase, lysosomal lipase, hepatic lipase, and lipoprotein lipase. Lipases function to cleave triglycerides into glycerol and free fatty acids, which are more readily bound by certain host molecules. This lipolytic activity may, for example, be included in fat-binding compositions containing cyclodextrin to improve the efficacy of the fat-binding composition, because cyclodextrins primarily bind the cleaved free fatty acids, and tend to bind uncleaved glycerol esterified fatty acids less. See Kashino et al., "Interaction of cyclodextrins with oily substances," *Nippon Kasei Gakkaishi*, 56(8), 533-539 (Japanese) 2005, the complete disclosure of which is hereby incorporated by reference for all purposes. Kashino et al. studied cyclodextrin binding of cholesterol and triolein, as well as lauric, myristic, palmitic, stearic, and oleic acid with alpha-cyclodextrin. It was found that alpha-cyclodextrin did not significantly bind cholesterol or triolein, but did bind oleic acid. Beta-cyclodextrin did significantly bind cholesterol, although the amount of beta-cyclodextrin involved was low, owing to poor solubility in water. Gamma-cyclodextrin was found to significantly bind oleic acid, cholesterol and triolein.

Preferred other components may include, for example, citric acid, ascorbic acid, and maltodextrin.

If the fat-binding composition is in solid form, the one or more other components each may be present in a concentration range of about 1-30% w/w or about 1-25% w/w. Preferably, the one or more other components each may be present in a concentration range of about 1-20% w/w or 1-15% w/w. More preferably, the one or more other components each may be present in a concentration range of about 2-5% w/w.

If the fat-binding composition is in the form of an aqueous beverage, the one or more other components may be present in a concentration range of about 1-20% w/v or about 1-15% w/v. Preferably, the one or more other components may be present in a concentration range of about 1-10% w/v or 1-5% w/v. More preferably, the one or more other components may be present in a concentration range of about 1-3% w/v.

VIII. Component Ratios

In addition to the above descriptions regarding the types and amounts of the various components that may be employed in the fat-binding composition disclosed herein, it is additionally noted that the relative amounts of these components can be described as well. Preferably, the weight ratio of the host molecule to the guest molecule may be in the range of about 5:1 to 1:10, more preferably may be in the range of about 2:1 to 1:5, still more preferably may be in the range of about 2:1 to 1:2, and yet more preferably may be in the range of about 1:1 to 1:2.

Regarding the other possible components, such as flavor components, carbonation-forming components, and other components described above, the weight ratio of the host molecule to each of the other components separately may be in the range of about 25:1 to 1:25, or about 10:1 to 1:10, or about 5:1 to 1:5, or optionally about 2:1 to 1:2, as well as 1:1.

IX. Processes of Forming the Inclusion Complex

The inclusion complex of the host molecule and the guest molecule can be formed by employing various methods.

Some exemplary methods for forming the inclusion complex may include combining the host molecule and guest molecule in a saturated solution, and heating the solution to a temperature in the range of about 50-60° C. In some cases, the solution may also contain a co-solvent besides water, such as a short chain alcohol. Non-limiting examples of co-solvents may include ethanol, isopropanol, acetone, ethyl-acetate, etc. The reaction time to form the inclusion complex may take a few hours, and sometimes between about four to eight hours. The saturated solution then may be cooled to cause crystallization of the inclusion complex. The crystalline product may be isolated by filtration and centrifugation. Filtration may be carried out by membrane layer filtration under vacuum, cartridge filtration under pressure, or filtration across sintered glass filters, etc., followed by a washing step, as discussed below. The crystalline product then may be dried to a constant weight. If dried in air, the product may have a relatively large particle size in the range of about 250-750 microns, for example. Alternatively, the crystalline product may be dried over an appropriate desiccant, such as $P_2O_5$ or KOH, or dried in a microwave drier, at room temperature to form a fine powder that may have an average particle size less than about 200 microns. As another alternative, the crystalline product may be dried in a vacuum oven at an elevated temperature, such as in the range of about 60-70° C., to form a fine powder.

An advantage of these exemplary processes is a low amount of adsorbed unbound guest molecule, due to a washing step after filtration. The desired product is a solid powder substantially constituting a proper guest-host inclusion complex with little or no unbound guest molecule adsorbed to the host molecules. The filtered wet inclusion complexes may be washed with cold (e.g. 4° C.) dioxane or n-hexane or diethylether to remove any surface bound guest. The product of this method also may exhibit desired crystalline properties and advantageously low moisture sorption properties, such that the equilibrium moisture content of the produced solid inclusion complexes can vary between only about 4-8 percent by weight. In some cases, a ternary complex may be obtained where solvent molecules play a role in maintaining the guest molecule in the cyclodextrin cavity. These processes may take about 24-48 hours, and may require the use of significant amounts of solvent and/or energy. Also, these processes may be limited to processes for forming inclusion complexes containing guest molecule that are not susceptible to decomposition at the reaction temperature employed. These types of processes may not be preferred for complexation of guest molecules with highly soluble cyclodextrin derivatives, such as methylated beta-cyclodextrins, 2-hydroxypropylated beta-cyclodextrins, and water soluble beta-cyclodextrin polymers.

Other examples of processes for forming the inclusion complexes of a host molecule and a guest molecule may include conducting the complexation process in a suspension, using a kneading or extrusion technique, or using a solid-phase technique, as described below.

Some exemplary suspension methods for forming inclusion complexes may include adding, to a reaction vessel, equimolar amounts of the host molecule and the guest molecule. Water, or a water-ethanol mixture with a low ethanol content (e.g. about 1 to 30% of ethanol), then may be added as a solvent. The amount of solvent may vary depending on the cyclodextrin component characteristics, but generally the amount can be about 3-10 times the weight of the sum of the weight amounts of both the host molecule and the guest molecule. For example, 10 grams of host molecule and 1 gram of guest molecule may be reacted in 30-100 grams of water or a water-ethanol mixture. The reaction mixture preferably may be stirred with a high-speed stirrer (e.g., an "ULTRA-TURRAX" stirrer made by IKA), or by the use of an ultrasonic mixing device, at room temperature for about 4-14 hours, depending on the selected guest molecule. These reactions may be monitored with a suitable endpoint-indicating method, for determining when the reaction has reached an endpoint. After the reaction has reached the endpoint, stirring may be stopped. The reaction mixture then may be subjected to one of the following alternative recovery techniques: (1) chilling to about minus 60° C. and removing the water by lyophilization; or (2) subjecting the reaction mixture to normal agitation and then spray-drying (e.g. using a device made by Niro or Buchi) or then evaporation by use of a fluid bed drying system, such as for example a Wurster type fluid bed process. The resulting solid product is preferably a molecularly dispersed, molecularly encapsulated inclusion complex with the host molecule serving as a "host" molecule and the guest molecule serving as a "guest" molecule.

Other processes for forming inclusion complexes in a suspension may include suspending (rather than dissolving) the host molecule in water, preferably by mixing, at approximately room temperature, or in the range of about 20-25° C., about one part host molecule with about two parts water. Stirring of the host molecule suspension preferably should be vigorous and may be a significant factor. A combination of typical vigorous stirring, e.g., at least about 600 rotations per minute, may be effective. The guest molecule, or guest, then may be added (either in its present form, or pre-dissolved in a solvent, such as ethanol or isopropanol) to the host molecule suspension. The reaction time may take on the order of about 4-24 hours, depending upon the type of host molecule(s) and guest molecule(s) used. The product inclusion complex then may be recovered from solution by filtration, such as is described above, by spray-drying such as is also described above, or by any other suitable method. These processes for forming inclusion complexes in a suspension may be advantageous, because relatively low amounts of energy and solvent may be consumed, and relatively high yields of product may be produced with relatively little prep-work (i.e., little "mother liquor" is formed). These processes also may be relatively easy to scale-up, as evidenced by the fact that similar processes are used industrially in countries such as the United States, Hungary and Germany. On the other hand, these suspension processes may require a lengthy stirring time period of 12-24 hours, and the ratio of adsorption to complexation of the guest molecule may be lower than desired.

Processes of forming inclusion compounds using kneading or extrusion techniques may include kneading the host molecule with water in order to "activate" it, with the approximate ratio of host molecule to water being within the range of about 1:1 to 2:1. The reaction temperature may be approximately room temperature in the range of about 22-25° C. The guest compound typically is not in solution when it is introduced into activated host molecule. The reaction time may be less than 60 minutes, depending upon the type of guest compound. Advantages of employing such kneading or extrusion techniques may include the absence of a requirement for using a solvent other than water, such that the final product may also be solvent free. The reaction time may be very fast, on the order of about one to two hours. The inclusion complex may have a relatively low crystalline character, due to the fact that the kneading used for "activation" may damage the crystalline lattice of produced cyclodextrin hydrate molecules. X-ray and DSC thermal analyses have shown that the resulting product is amorphous, with a high rate of complexation of the guest molecules, and without the formation of mother liquor. This process may be useful for all types of cyclodextrins and derivatives thereof. Also, these processes may be generally acceptable from an environmental standpoint. Similar methods have been employed in Japan on an industrial scale. These methods may require a proper kneading machine, such as a twin screw extruder, for example, and it may be somewhat difficult to remove the wet product from the machine at the conclusion of the process.

Conducting complexation processes using solid-phase techniques may require both the host molecule and guest compound to be in solid form. These components may be subjected to high energy milling, intense co-grinding, or any other suitable method. Critical factors may include the intensity of the mechanical energy and the moisture content of the cyclodextrin. For example, a content of less than about 2-3% water inhibits or prevents cyclodextrin from complexing. The advantages of using a solid-phase technique may include the flexibility of employing any type of host molecule, without requiring a solvent other than water, and with an advantageously short reaction time. Also, scaling up easily may be done and, with no "mother liquor" being formed, there may be environmental advantages. In addition, the rates of dissolution of complexed drugs generally may be higher than that of other methods. Disadvantages may include the formation of metastable solid phases (complexes), which may recrystallize upon storage reaching the equilibrium state.

Processes for preparing inclusion complexes involving host molecules, such as cyclodextrin derivatives, may employ a homogeneous reaction that proceeds at room temperature, wherein the components are dissolved in water or a water/co-solvent mixture. The product may be obtained by an evaporation, spray-drying, or freeze-drying technique.

Additional examples of processes and process parameters which can be used to form the inclusion complexes may correspond to those disclosed in: (1) L. Szente, "Preparation of Cyclodextrin Complexes" in "Comprehensive Supramolecular Chemistry," Vol. 3, *Cyclodextrins*, Edit. J Szejtli and T Osa, Elsevier Science, Pergamon Press, 1996, pages 243-251; (2) Szejtli, J., *Cyclodextrin Technology*, Kluwer Academic Publishers, Dordrecht, The Netherlands, 1988, pages 80-104; and (3) Szejtli, J., *Cyclodextrins and Their Inclusion complexes*, Akademiai Kiado, Budapest, 1982, pages 95-110, the complete disclosures of which are hereby incorporated by reference for all purposes which are all Processes for forming inclusion complexes containing amylose may include first preparing an alkaline aqueous solution (e.g., pH about 12) containing amylose, preparing an alcohol solution containing the guest molecule, and adding the alcohol solution to the alkaline solution with vigorous agitation at room temperature to form a reaction mixture. The reaction mixture then may be neutralized, while stirring, by the addition of an acid, such as hydrochloric acid. The neutralized reaction mixture may contain precipitate, which may be stirred for about five hours to obtain formation of the inclusion complex. The inclusion complex may be insoluble, and may be filtered from the reaction mixture as generally described above. The wet solid complex may be washed with cold dioxane or other suitable washing solvent, and then may be dried (such as in a vacuum at or about 100° C.) until the inclusion complex product achieves a constant weight, also as described above. See Szejtli, J et al. Acta Chim. Acad. Sci. Hung., 1979, 99 (4), 447-52, the complete disclosure of which is hereby incorporated by reference in its entirety for all purposes.

X. Selected Exemplary Embodiments

Selected embodiments of the fat-binding compositions disclosed herein may include liquids, solutions, or instantly-soluble solid forms of the fat-binding compositions described above. For example, wettable and/or rapidly dissolvable powders, as well as carbonated water products prepared from such powders or otherwise containing the aforementioned inclusion complexes are preferred embodiments. These embodiments advantageously may inhibit self-aggregation of any cyclodextrin component that is present due to the effect of the carbonation. Other preferred embodiments of fat-binding compositions may include inclusion complexes with cyclodextrins, and also may include aggregation-preventing compounds, such as hydroxyl-acids, such as citric acid, succinic acid, tartaric acid, malic acid, etc. The cyclodextrin components of these fat-binding compositions advantageously may be inhibited from undergoing self-aggregation in situ.

The following examples are provided as illustrations, and are not intended to limit the scope of this disclosure in any way.

EXAMPLES

Example 1—Example of Fat Binding by Cyclodextrins in Aqueous Environment

An aqueous cyclodextrin solution was prepared by dissolving a mixture of alpha-, beta- and gamma-cyclodextrins (composed of 9.7 grams of alpha-cyclodextrin, 11.3 grams of beta-cyclodextrin, and 12.7 grams gamma-cyclodextrin), at a concentration of 0.01M, in one liter of deionized water solution of 2.5 grams of palmitic acid in 5 mL of diethylether was added drop-wise to the aqueous cyclodextrin to reach a concentration level of 0.01M. This reaction mixture was stirred for four hours at ambient temperature. The reaction mixture produced a white suspension. The precipitate was removed by centrifugation. The precipitate is a crystalline inclusion complex of palmitic acid complexed with the cyclodextrins. The resulting complex contains: about 78% of alpha-cyclodextrin/palmitic acid complex, about 20% of beta-cyclodextrin/palmitic acid complex, and undetectable amounts of gamma-cyclodextrin/palmitic acid complex. This example shows that among alpha-, beta- and gamma-cyclodextrins, the most suitable type for immobilizing and entrapping a linear, saturated fatty acid, like palmitate, is alpha-cyclodextrin, followed by beta-cyclodextrin. The result for gamma-cyclodextrin in this particular example is negligible.

Example 2—Example of Inclusion Complex Process Description Using Beta-Cyclodextrin A cyclodextrin inclusion complex can be produced in an aqueous suspension at room temperature, with or without co-solvents or additives that may be used depending upon the aqueous solubility of the guest molecule. The inclusion complex-forming reaction may be conducted in a glass or stainless steel reactor equipped with a suitable stirring device. A solution was prepared by dissolving, at room temperature, 100 grams of a guest molecule (e.g. carnitine having a molecular mass of about 160 Daltons) in 300 milliliters of water or in a suitable water miscible solvent, such as ethanol, isopropanol, propyleneglycol, or a polyethyleneglycol. Separately, in the reactor, 1.50 kg of beta-cyclodextrin was suspended in 2.5 liters of purified water with vigorous stirring at room temperature. The solution of the guest molecule was added drop-wise to the beta-cyclodextrin aqueous suspension while the stirring continued at a level of over about 600 rpm (rotations per minute). The reaction mixture was continuously stirred at 600 rpm for about three hours at room temperature. Subsequently, the water content of the suspension was removed by spray-drying to obtain solid powder. The spray-drying was performed under the following operating conditions using a spinning head spray-dryer (manufacturer: Niro):
  input temperature: about 180-200° C.
  output temperature: 90-95° C.
  spinning rate: 20,000-22,000/minute
  spray-drying time: about 40 minutes This process yielded about 1.5 kg of a solid powder form inclusion complex with a residual water content of about 6-8% by weight.

Example 3—Exemplary Fat-Binding Composition

One kilogram of bulk solid powder was formed which contained:
  427.5 grams of anhydrous citric acid
  121.0 grams of ground sodium-carbonate
  46.0 grams of sodium bicarbonate
  4.6 grams of ascorbic acid
  5.4 gram of xylitol (made from corn fibers)
  350 grams of spray-dried alpha-cyclodextrin/L-arginine inclusion complex
  10.0 grams of grape or lemon or orange spray-dried flavor/maltodextrin
  0.5 gram colorant The above composition, when dissolved in non-carbonated water, produced significant effervescence, was a transparent solution and had a pleasant, tasteful acidity (pH of about 5.3).

Example 4—Exemplary Fat-Binding Composition

One kilogram of bulk solid powder was formed which contained:
  435 g of anhydrous citric acid
  183 g of anhydrous sodium carbonate
  23 g sodium bicarbonate
  21.7 g ascorbic acid
  7 g of xylitol
  210 g of nicotinamide/alpha-cyclodextrin complex, spray-dried (with 8% nicotinamide content by weight)
  120 g of orange flavour/alpha-cyclodextrin complex (with a 12% orange flavour load by weight)
  0.3 g of colorant

Example 5—Exemplary Effervescent Fat-Binding Composition

Below is an example an effervescent formulation including taurine and creatine as guest molecules which provide nutritional benefits and act to prevent cyclodextrin aggregation in water.

| Effervescent Formulation Components | Amounts in grams |
| --- | --- |
| Taurine | 10 |
| Creatine | 20 |
| Sodium bicarbonate | 10 |
| Citric acid + ascorbic acid | 15 + 2 |
| Potassium carbonate | 1.5 |
| Niacinamide | 0.5 |
| Carnitine | 1.0 |
| Sorbitol or xylitol sweetener | 0.3 |
| Strawberry flavor | 1.25 |
| Colorant (riboflavin) | 0.2 |
| Dextrose | 35 |
| Cyclodextrin | 5 |

Example 6—Stability Study of Compositions of Examples 3 and 4

The compositions of Examples 3 and 4 above were packed, immediately after being produced, into an air-tight triple-layer bag, having an aluminum foil layer disposed between two polyethylene plastic layers. The bags were kept at room temperature for 30 days. No noticeable degradation or carbon-dioxide gas evolution was observed. This exhibited stability is significant, because the tested bulk solid compositions were shown to not be susceptible to reacting with any available moisture so as to initiate the chemical reaction leading to undesired generation of carbon dioxide gas within the sealed bags.

Example 7—Analysis of Inclusion Complex Containing Betanin

An inclusion complex including alpha-cyclodextrin and betanin as a guest molecule was prepared as follows:
In a reaction vessel, 550 grams of betanin was dissolved in two liters of deionized water at room temperature under continuous agitation. Then 1000 grams of crystalline alpha-cyclodextrin hydrate was added in ten 100 gram portions to the stirred reaction mixture. After the alpha-cyclodextrin was added to the reaction mixture, the resulting dense suspension was further stirred for 4 hours at room temperature. The reaction mixture was allowed to dry under normal conditions in air to a constant weight, and was then ground to fine powder with a ball mill.

The resulting 1:1, molar ratio betanin/alpha-cyclodextrin inclusion complex was a red colored, free flowing powder containing 32% betanin by weight, as determined by visible spectrophotometry. The betanin/alpha-cyclodextrin complex was found to be a relatively weak inclusion complex in water as determined by phase-solubility studies according to Higuchi et al., *Advances in Analytical Chemistry and Instrumentation*, edited by C. N. Reilly, Wiley, New York, 1965.

vol. 4. pp. 117-212, the complete disclosure of which is hereby incorporated by reference for all purposes. The binding constant of the complex was $K_{ass}$=85-105 $M^{-1}$ A characterization of the free- and entrapped (or complexed) betanin in the solid state was performed by comparing the thermo-analytical behavior of the colorant outside and within the inclusion complex. The colorant (glycopyranosyl dihydro indolyl-pyridine carboxylic acid, extracted from beets) characteristically shows a low temperature phase transition upon heating in an argon atmosphere. This thermal event, characteristic for betanin, typically occurs at 85-120° C. according to a differential scanning calorimetry (DSC) assay. However, this thermal event shifted significantly to a much higher temperature range of 170-200° C. when the betanin was complexed with alpha-cyclodextrin, indicating that the phase transition (i.e. the transition from solid to liquid or the melting or the glassy transition) occurs at higher temperature if the colorant is not in a highly-ordered, nearly crystalline lattice, but is included in the inclusion complex so as to be molecularly dispersed and so as to melt together with the cyclodextrin carbohydrate matrix.

Example 8—Comparison of Fat Binding Properties of Host Molecules with and without Inclusion Complex Two types of solid alpha-cyclodextrin formulations were prepared as follows.

Formulation 1

Crystalline α-cyclodextrin hydrate was formulated into a tablet by using common tabletting additives as follows:

| | |
|---|---|
| α-cyclodextrin hydrate | 97 parts by weight |
| Magnesium stearate | 2.5 parts by weight |
| Light silicic anhydride | 0.5 part by weight |

The bulk blend containing the above components was granulated in a Frewitt granule machine by wetting the dry blend with an isopropyl-alcohol and water mixture, followed by drying at 45° C. in trays. The granule was then pressed into tablets weighing one gram.

Formulation 2

The same amount of alpha-cyclodextrin hydrate as used in Formulation 1 above was wetted with water and intensively co-ground for 30 minutes in a ceramic mortar with a weak complex-forming free base form of L-arginine and crystalline citric acid, without the addition of any magnesium stearate. This co-ground, wet arginine-citric acid-cyclodextrin ternary inclusion complex was dried in air to a constant weight. The dry inclusion complex was re-wetted and granulated in a conventional granulating setup and dried in air at 45° C. to constant weight. The granules had the following composition:

| | |
|---|---|
| α-cyclodextrin hydrate | 97 parts by weight |
| L-Arginine | 2.5 parts by weight |
| Citric acid | 0.5 part by weight |

The granules were filled into sachets each containing one g of Formulation 2.

A comparison of Formulations 1 and 2 was then conducted. One gram amounts of each of Formulations 1 and 2 were introduced into 500 mL portions of each of: (1) 0.01 N hydrochloric acid with a pH of 2; and (2) an aqueous buffer solution with a pH 7.2. The temperature was set at 37° C. After stirring at 90 rotations per minute for 2 hours, the resulting solutions were tested for concentrations of dissolved alpha-cyclodextrin by using the HPLC method. Formulation 1, the tabulated alpha-cyclodextrin containing product, produced an opaque, non-transparent solution after two hours of stirring. This indicated that the alpha-cyclodextrin did not significantly dissolve. Formulation 2, the granules containing citric acid, L-arginine and alpha-cyclodextrin hydrate, immediately dissolved to produce a clear, transparent solution.

Table 1 below shows the measured dissolved amounts of alpha-cyclodextrin from Formulations 1 and 2 after subjecting these formulations to the conditions described above. As is clear from the results, Formulation 2 provided significantly more alpha-cyclodextrin in both the acidic and basic aqueous environments than did Formulation 1. The dissolved amounts of cyclodextrin correspond to cyclodextrin molecules available for fat binding.

TABLE 1

Dissolved Cyclodextrin Values

| | Dissolved amount of alpha-cyclodextrin (%) in different dissolution media determined by HPLC | |
|---|---|---|
| Tested Samples | gastric medium (pH 2) | intestinal medium (pH 7.2) |
| Formulation 1 Tablet with Mg-stearate | 35.8 | 46.8 |
| Formulation 2 Granules with Arginine and citric acid | 100 | 89.9 |

The above data from Formulation 1 indicate that the presence of even small amounts of a fat-related additive, such as the fatty acid magnesium stearate, can significantly reduce the availability for dissolution in an aqueous environment of a cyclodextrin, and thus can reduce the amount of cyclodextrin available for binding fat and fat-related compounds. In contrast, the data from Formulation 2 indicate that employment of an inclusion complex of a cyclodextrin with a guest molecule can result in efficiently providing a significant amount of the cyclodextrin, e.g. up to 100%, that is available for fat binding in both acidic and basic aqueous environments.

Example 9—Binding Constants for Various Flavorants

In order to analyze whether various flavorants and related compounds exhibit appropriately weak complex-forming properties, several examples were complexed with alpha- and beta-cyclodextrin, and the exhibited binding constants thereof were measured. The tested compounds included those that are generally soluble or miscible in water. The complexes with the cyclodextrins were formed using methods corresponding to the two specifically described examples below involving apricot flavorant and banana flavorant.

A. Preparation of Apricot Flavorant/Alpha-Cyclodextrin Complex by Spray Drying 972 grams of alpha-cyclodextrin hydrate was dispersed in 500 mL of water at room temperature by vigorous stirring. The slurry was diluted with an additional 500 mL of water. To the stirred alpha-cyclodextrin water mixture, 12 grams of apricot flavorant was added drop wise during intense agitation. Once the flavorant was completely added to the reaction mixture, the mixture was stirred for an additional four hours at room temperature. The reaction mixture was fed to a Buch Laboratory spray-drier to remove water. The spray-drying conditions were as follows:

input temperature: about 170-190° C.
output temperature: 85-90° C.
spinning rate: 20,000-22,000/minute The resulting 955 grams of free-flowing white powder contained about 9.4% w/w apricot flavorant as determined by Gas Chromatography.

B. Preparation of Banana Flavorant/Beta-Cyclodextrin Complex by Kneading 1135 grams (one mole) of beta-cyclodextrin was wetted with 250 grams of water at room temperature in a twin screw kneader by continuous cycling. To the wet mechanically activated beta-cyclodextrin, 120 grams of banana flavorant concentrate was added through a feeding funnel during a 15 minute period, while continuously kneading the mixture. The kneading was maintained for 45 minutes, then the resulting wet banana flavorant beta-cyclodextrin complex was removed and dried at 45° C. in stainless steel trays to constant weight. The resulting product was ground to a fine powder. 985 grams of fine powder was obtained. The banana flavorant content was about 8.8% by weight as determined by Gas Chromatography.

The results of binding constant measurements for the above flavorants, as well as other examples, are shown in Table 2 below.

TABLE 2

Calculated Binding Constants of Some Flavorants and Related Compounds

Guest molecules: Calculated Binding Constants ($M^{-1}$)

| Flavorants and Related Compounds | Complex formed with alpha-cyclodextrin | Complex formed with beta-cyclodextrin |
|---|---|---|
| apple flavorant | 65 | 40 |
| Butyl acetate | 72 | 85 |
| butyl isovalerate | 95 | 110 |
| allyl butyrate | 45 | 34 |
| Apricot flavorant | 98 | 70 |
| amyl valerate | 67 | 45 |
| Ethyl acetate | 60 | 100 |
| ethyl valerate | 46 | 80 |
| Banana flavorant | 90 | 120 |
| Amyl acetate | 85 | 40 |
| maltol | 70 | 98 |

Two types of methods were used to determine the apparent binding constants noted above. The "microcalorimetric" method was used as described in Lewis et al., "Thermodynamics of binding of guest molecules to alpha- and beta-cyclodextrins," *J. Chem. Soc. Perkin. Trans.* 2, (15) pp. 2081-2085, 1973, the complete disclosure of which is hereby incorporated by reference for all purposes. Also, by measuring the flavorant retention in the inclusion complexes and the corresponding mechanical mixtures (identical composition except that linear dextrin is used in place of cyclodextrins) with gas chromatography, according to the method described by Reineccius et al., "Encapsulation of flavors using cyclodextrins: comparison of flavor retention in alpha, beta, and gamma types," *Journal of Food Science*, 67(9), pp. 3271-3279 (2002), the complete disclosure of which is hereby incorporated by reference for all purposes.

Example 10—Preparation of alpha-cyclodextrin Inclusion Complex with N-tertiary-butyl-hydroxylamine 975 grams of alpha-cyclodextrin hydrate was dissolved in one liter of deionized water at 25° C. with vigorous stirring. To the resulting clear solution, 98 grams of N-tert-butyl-hydroxylamine was added while continuously and intensively stirring the reaction mixture. After two hours of stirring, the reaction mixture was chilled to minus 55° C. and the water was removed by freeze-drying. 1,050 grams of the lyophilized solid complex was obtained. The hydroxylamine incorporation into the alpha-cyclodextrin matrix was 9.0% by weight, as determined by HPLC. The residual water content in the lyophilized product was 3.4%, as determined by Karl-Fisher titrimetry.

Also, the apparent binding constant of the alpha-cyclodextrin N-tert-butyl-hydroxylamine complex was determined by chromatography. The binding constant was found to be 80-105 $M^{-1}$ for the above alpha-cyclodextrin/hydroxylamine inclusion complex in water at 25° C. These results show that such complexes can be produced in a stable solid form and dissolved in water for release of the N-alkyl-hydroxylamine compound to exert its advantageous antioxidant and anti-aging effects, and for release of the cyclodextrin compound to exert its advantageous fat binding effects.

Example 11—Preparation of Host Molecule Inclusion Complexes with Colorants

A. Preparation of Amylose Inclusion Complex with Colorant:

100 grams of amylose (DP=250, manufacturer AVEBE Netherlands) was stirred in 450 mL of an alkaline aqueous solution at pH 12.2 at room temperature. Under vigorous stirring 12 grams of a natural colorant mixture extracted from blue grapes dissolved in 10 mL of 96% ethanol is added to the stirred amylose solution. The pH of reaction mixture is set to neutral by drop wise feeding 2N hydrochloric acid under stirring. The neutralized reaction mixture turned into a dense suspension. This suspension was stirred for an additional four hours to complete colorant complexation. The formed complex was isolated by centrifugation. The wet solid product was dried in air to a constant weight and ground to a fine powder. A yield of 108 grams of a purple colored amorphous solid complex was obtained. The colorant content of the complex was 9.6% by weight as determined by HPLC/UV-VIS detection.

B. Preparation of Beta-Cyclodextrin Complex with Colorant 13.35 grams of crystalline beta-cyclodextrin was kneaded in 250 mL of water for 30 minutes to produce wet ground activated cyclodextrin. 150 grams of a natural beetroot extract having a 90% betalain content was added to the activated cyclodextrin in an aqueous solution. The reaction mixture was further kneaded in a twin-screw kneader for two hours at ambient room temperature. The resulting wet semisolid was dried in air to a constant weight for a yield of 1100 grams of red powder. The colorant content was 9.6% by weight as determined by spectrophotometry.

Example 12—Preparation of Amylose Inclusion Complex with Flavorant 55 grams of amylose (DP=250, manufacturer AVEBE) was preliminarily swollen with slow stirring in an alkaline solution having a pH of 12 for three hours at room temperature. The alkaline solution was heated to 60° C. under continuous stirring and was neutralized with 2N hydrochloric acid while stirring for five minutes. The neutral amylose solution was further continuously stirred at 40° C. while five grams of strawberry flavor concentrate was added drop wise to the amylose solution. The reaction mixture was cooled to room temperature during stirring and the precipitate that formed was filtered off. The wet solid amylose/strawberry flavor complex was dried in air to a constant weight. The yield was 52 grams of white or off white solid with a slight strawberry aroma. The flavor content of the complex was determined by headspace Gas Chromatography and found to be 8.8% by weight.

Example 13—Determination of the Association Constants or Binding Constants of Selected Cyclodextrin Complexes The equilibrium constant for the formation of an inclusion complex is a fundamental measure of the stability of the complexes relative to the separated species, under given conditions (temperature, medium, pressure etc.). The terms of association- or binding- or stability- or formation-constants are synonymous.

The numeric values of association constants refer primarily to the ratio between included (cavity residing) fraction of guest substances over the non-complexed fraction. The extent of inclusion of a guest substance by the host cyclodextrin—under given conditions—will be in a positive correlation with the association constant. The higher the stability constants the larger portion of total guest molecules will be bound into the cyclodextrin cavities.

The association or binding constants of several selected weak complex-forming guest molecules with alpha-, beta- and gamma-cyclodextrins were experimentally determined. Capillary electrophoresis was utilized to determine the complex binding constants of selected dietary supplements thiamine, niacin and L-arginine in aqueous systems. The following values were determined:

TABLE 3

Association Constants of Dietary Supplement Complexes

|  | α-Cyclodextrin | β-Cyclodextrin | γ-Cyclodextrin |
|---|---|---|---|
| L-arginine | 21 ± 2* | 100 ± 5 | 9 ± 2 |
| Thiamine HCl | 20 ± 2 | 73 ± 3 | 8 ± 1 |
| Nicotinic acid | 17 ± 2 | 37 ± 3 | 10 ± 2 |

*The listed association constant values represent a mean of three parallel determinations with acceptable standard deviations.

Similarly, capillary electrophoresis was utilized to determine the complex binding constants of selected flavorants ethyl acetate, isoamyl acetate, diacetyl, and N,N-dimethyl formamide with alpha-, beta- and gamma-cyclodextrins. The following values were determined:

TABLE 4

Active Ingredient Content of Selected Flavorant Complexes

|  | Average (%) | RSD % | Water Content (%) |
|---|---|---|---|
| isoamyl acetate |  |  |  |
| β-Cyclodextrin | 8.8 | 3.8 | 4.0 |
| α-Cyclodextrin | 8.5 | 4.5 | 4.2 |
| γ-Cyclodextrin | 11.4 | 4.7 | 6.5 |
| diacetyl |  |  |  |
| β-Cyclodextrin | 1.3 | 4.8 | 9.2 |
| α-Cyclodextrin | 0.9 | 4.4 | 7.3 |
| γ-Cyclodextrin | 1.3 | 4.6 | 8.1 |
| ethyl acetate |  |  |  |
| β-Cyclodextrin | 0.6 | 3.7 | 4.1 |
| α-Cyclodextrin | 4.1 | 4.3 | 6.0 |
| γ-Cyclodextrin | 0.1 | 4.9 | 3.1 |

Among the exemplified flavor substances, isoamyl acetate forms an inclusion complex with the selected cyclodextrins in a molar stoichiometry close to the theoretical 1:1 molar ratio.

The following claims encompass selected and exemplary aspects of the fat-binding compositions disclosed herein. These claims may encompass multiple distinct inventions with independent utility, and are in no way intended to limit the scope of the invention.

TABLE 5

Association Constants of Selected Flavorant Complexes

|  | K (1/M) | RSD % |
|---|---|---|
| isoamyl acetate |  |  |
| α-Cyclodextrin | 729 | 8.4 |
| β-Cyclodextrin | 382 | 10.9 |
| γ-Cyclodextrin | 32 | 10.0 |
| diacetyl |  |  |
| α-Cyclodextrin | 28 | 33.4 |
| β-Cyclodextrin | 43 | 16.4 |
| γ-Cyclodextrin | 58 | 13.8 |
| ethyl acetate |  |  |
| α-Cyclodextrin | 37 | 13.7 |
| β-Cyclodextrin | 10 | 31.6 |
| γ-Cyclodextrin | 9 | 30.9 |

These experimentally determined and relatively low binding constants for selected guest-cyclodextrin inclusion complexes confirm that in the presence of fatty acids, the relatively weakly associated guest molecules would be replaced by fatty acid molecules, as the corresponding fatty acid-cyclodextrin inclusion complexes exhibit binding constants in the range of 500-5000 1/M.

Although the present invention has been shown and described with reference to the foregoing operational principles and preferred embodiments, it will be apparent to those skilled in the art that various changes in form and detail may be made without departing from the spirit and scope of the invention. All novel and non-obvious combinations and subcombinations of the elements, features, functions, and properties described and/or illustrated herein should be recognized as being included within the scope of this disclosure. Applicant reserves the right to claim one or more of the inventions in any application related to this disclosure. The present invention is intended to embrace all the alternatives, modifications and variances that fall within the scope of the appended claims.

What is claimed is:

1. A fat-free food product composition for consumption by an animal, comprising:
   a first guest-host inclusion complex of a host molecule that is an α- or β-cyclodextrin without a fatty molecule; and a first guest molecule that is a dietary supplement, a flavor enhancer, or aroma enhancer;
   wherein the binding constant of the guest-host inclusion complex is 10-100 $M^{-1}$ and the binding constant of the complex of the same host molecule and a fatty acid is 500-5000 $M^{-1}$
   wherein the first guest molecule is weakly and reversibly associated with the host molecule, and wherein the first guest molecule is selected from the group consisting of: niacin and niacin derivatives, arginine, thiamine, and N-alkyl $C_1$-$C_3$ and N-acetylated $C_1$-$C_3$ derivatives thereof, betanin, apple flavorant, apricot flavorant, banana flavorant, butyl acetate, butyl isovalerate, allyl butyrate, amyl valerate, ethyl acetate, ethyl valerate, amyl acetate, maltol, isoamyl acetate, diacetyl, N—$C_1$-$C_4$-alkyl-hydroxylamine, and appropriate salt or hydrate forms thereof; and
   wherein the composition does not contain either fat or fat-derived components.

2. The food product composition of claim 1, wherein the composition further comprises a food product that is a fat-free beverage.

3. The food product composition of claim 1, wherein the composition is water soluble and further comprises a dry, fat-free solid.

4. The food product composition of claim 1, wherein the composition further comprises a starch-containing, fat-free food product.

5. A fat-free composition for preparing a beverage to be consumed by an animal, comprising:
   a guest-host inclusion complex of a host molecule that is an α- or β-cyclodextrin without a fatty molecule; and a first guest molecule that is a dietary supplement, a flavor enhancer, or aroma enhancer;
   wherein the binding constant of the guest-host inclusion complex is 10-100 $M^{-1}$ and the binding constant of the complex of the same host molecule and a fatty acid is 500-5000 $M^{-1}$;
   wherein the first guest molecule is weakly and reversibly associated with the host molecule, and wherein the first guest molecule is selected from the group consisting of: niacin and niacin derivatives, arginine, thiamine, and N-alkyl $C_1$-$C_3$ and N-acetylated $C_1$-$C_3$ derivatives thereof, betanin, apple flavorant, apricot flavorant, banana flavorant, butyl acetate, butyl isovalerate, allyl butyrate, amyl valerate, ethyl acetate, ethyl valerate, amyl acetate, maltol, isoamyl acetate, diacetyl, N—$C_1$-$C_4$-alkyl-hydroxylamine, and appropriate salt or hydrate forms thereof; and
   wherein the composition does not contain either fat or fat-derived components.

6. The composition of claim 5, wherein the composition is a dry solid, and the addition of water to the composition yields the beverage.

7. The composition of claim 6, wherein the composition is in the form of a tablet, pellets, granules, or a powder.

8. The composition of claim 7, wherein the composition further comprises a powder that produces an effervescent beverage upon the addition of water.

9. A method of preparing a fat-free food product composition for consumption by an animal that utilizes the fat-free food product composition of claim 1; the method comprising:
   a) combining the host molecule and the first guest molecule under conditions suitable for forming the guest-host inclusion complex;
   b) purifying and isolating the first-guest-host inclusion complex;
   c) selecting other fat-free food product components; and
   d) combining the purified guest-host inclusion complex with the other fat-free food product components to produce a food product composition.

10. The method of claim 9, wherein purifying the guest-host inclusion complex further comprises removing uncomplexed guest molecules.

11. The method of claim 9, wherein combining the host molecule and the guest molecule further comprises preparing a solution, suspension, or slurry.

12. The method of claim 9, wherein combining the host molecule and the guest molecule further comprises a dry blending process.

13. The method of claim 9, wherein the combining the host molecule and the guest molecule further comprises preparing a saturated solution; and purifying the guest-host inclusion complex includes crystallization and filtration of the inclusion complex.

14. A method of reducing the fat available to be absorbed by the digestive tract of an animal in need thereof, where the animal has one or more fatty molecules within its digestive tract, comprising:
   selecting a food product that comprises a fat-free food product composition of claim 1;
   choosing the host molecule and first-guest molecule such that, within the animal's digestive tract, the first-guest molecule is substantially released from the host molecule, and the host molecule forms a nearly irreversible-second-guest-host inclusion complex with a fatty molecule that is present in the animal's digestive tract; and
   providing the food product to an animal for subsequent ingestion and ultimate digestion, resulting in release of the first-guest molecule, formation of the nearly irreversible-second-guest-host-inclusion complex, and exit of the latter in the waste of the animal,
   thereby removing the second-guest-host-inclusion complex, containing the fatty molecule from the digestive tract.

15. The method of claim 14, wherein supplying a food product comprises supplying a food product composition that is a beverage, or is a dry solid that produces a beverage when combined with water.

* * * * *